US007322350B2

(12) United States Patent
Kling

(10) Patent No.: US 7,322,350 B2

(45) Date of Patent: Jan. 29, 2008

(54) COMPRESSED AIR SUPPLY SYSTEM FOR A COMPRESSED AIR RESPIRATORY DEVICE

(75) Inventor: Peter Kling, Berlin (DE)

(73) Assignee: MSA Auer GmbH, Berlin (DE)

( * ) Notice: Subject to any disclaimer, the term of this patent is extended or adjusted under 35 U.S.C. 154(b) by 545 days.

(21) Appl. No.: 10/501,123

(22) PCT Filed: Dec. 21, 2002

(86) PCT No.: PCT/DE02/04688

§ 371 (c)(1), (2), (4) Date: Jan. 18, 2005

(87) PCT Pub. No.: WO03/058099

PCT Pub. Date: Jul. 17, 2003

(65) Prior Publication Data

US 2005/0115560 A1 Jun. 2, 2005

(30) Foreign Application Priority Data

Jan. 11, 2002 (DE) ................................ 102 01 250

(51) Int. Cl.
*A61M 11/00* (2006.01)

(52) U.S. Cl. ........................... 128/200.24; 128/205.23; 128/204.18

(58) Field of Classification Search ........... 128/205.23, 128/204.18, 205.22, 200.24
See application file for complete search history.

(56) References Cited

U.S. PATENT DOCUMENTS 4,498,471 A * 2/1985 Kranz et al. ........... 128/204.26
5,529,096 A * 6/1996 Rowe et al. .................. 141/21
6,070,577 A * 6/2000 Troup .................... 128/205.22

FOREIGN PATENT DOCUMENTS

FR 1152107 * 2/1955
FR 2733960 * 11/1996

* cited by examiner

*Primary Examiner*—Steven O. Douglas
(74) *Attorney, Agent, or Firm*—Wood, Phillips, Katz, Clark & Mortimer

(57) ABSTRACT

In a compressed air breathing apparatus, a single combined high/medium-pressure line (8) consisting of a medium-pressure hose and a coaxial, flexible high-pressure line inside said hose is integrated into the pressure reducer (5) connected to a compressed air bottle so that said line can rotate in axial direction. The free end of the combined high/medium-pressure line (8) can also rotate in axial direction when connected to a manifold block (9) for distributing the supplied high or medium-pressure air to connections for a lung machine (11), a pressure gauge (15), and an alarm whistle (17) that is controlled at high pressure and operated at medium pressure. The manifold block (9) is equipped with an additional high-pressure fast-fill connection (14) and an additional medium-pressure connection (13). A compressed air breathing apparatus of this design is simple, convenient, and safe to handle.

31 Claims, 3 Drawing Sheets

COMPRESSED AIR SUPPLY SYSTEM FOR A COMPRESSED AIR RESPIRATORY DEVICE

The invention relates to a compressed air supply system for a compressed air breathing apparatus with a pressure reducer connected to the compressed air bottle and pressure lines connected to the high-pressure and medium-pressure outputs of said pressure reducer.

In known compressed air breathing apparatuses, a compressed air bottle is mounted to a base plate held by a tensioning strap and by the connection to a pressure reducer. The pressure reducer comprises multiple outputs for conducting air at a high pressure that matches the pressure in the bottle to a pressure gauge or at a reduced medium pressure to a lung machine connected to a breathing mask. Pressure lines that branch off the high pressure and medium-pressure lines are used as high-pressure fast-fill or secondary medium pressure connections. An acoustic warning device is connected to another pressure line from the pressure reducer. Each pressure line is firmly connected to the pressure reducer and to the devices connected to their free ends.

This type of compressed air supply is disadvantageous as the multiplicity of pressure lines is an obstacle to rescue workers when putting on the compressed air breathing apparatus and during rescue operations. There is a risk to get caught on something, and the hoses can become entangled or twisted which limits the wearer's mobility. If a high-pressure line is damaged, much air is lost before the valve at the compressed air bottle is closed. Handling a compressed air breathing apparatus with such a compressed air supply system can also be difficult because the fittings for the pressure gauge, lung machine, alarm whistle, etc. are not located at the same point on the wearer's front.

It is therefore the problem of this invention to design a compressed air supply system of a compressed air breathing apparatus in such a way that wearing comfort, ease of putting the apparatus on and handling it are improved.

This problem is solved according to the invention by a compressed air supply system comprising the characteristics described in claim 1.

The general concept of the invention is a single-piece combined high-pressure and medium-pressure line the ends of which can be connected to the pressure reducer and to a manifold block placed at the front of the wearer with multiple outputs for air conducted into it at high and medium pressures by rotating said line in axial direction. High or medium-pressure outputs on the manifold block can be connected to a lung machine, a pressure gauge and an acoustic warning device or be used as secondary medium-pressure or high-pressure fast-fill fittings.

With such a compressed air supply and distribution system, all compressed air outputs and the connected measuring instruments, alarm devices, etc. are located at one and the same place within the wearer's range of vision and handling. This considerably simplifies handling of the apparatus. In addition, only a single combined high and medium-pressure line is connected to the pressure reducer. This makes using the compressed air breathing apparatus still easier. There is no maze of lines, and even the single remaining compressed air line that can easily be conducted along the back strap cannot be twisted as it is pivoted in axial direction both in the manifold block and in the pressure reducer by means of a rotary coupling. As the acoustic alarm device connected to the manifold block can use both high-pressure as well as medium-pressure air, it can be advantageously controlled using high-pressure air but operated using medium-pressure air to produce a long-lasting acoustic alarm signal with sufficient sound volume.

According to another characteristic of the invention, the combined high-pressure/medium-pressure line is designed as a coaxial line so that a spirally wound flexible high-pressure line is arranged inside a medium-pressure hose made of flexible material as well. If the high-pressure line breaks, the rapidly leaking compressed air does not immediately escape into open air but into the medium-pressure line that is secured by a pressure relief valve, and the wearer can still inhale and exhale it.

In another embodiment of the invention, the rotary coupling that pivotably connects the combined high/medium-pressure line to the manifold block on one end and to the pressure reducer on the other comprises a connecting nozzle for the medium-pressure hose and a high-pressure connecting nozzle sealed gastight against each other and pivoted in the manifold block or the manifold body of the pressure reducer, respectively, and connected to a medium-pressure duct or high-pressure duct, respectively, in the manifold block/manifold body. Expanded compressed air can flow into the medium-pressure hose and high-pressure air can flow into the high-pressure line and from these into the manifold block in each rotational position of the high/medium-pressure line or the rotary coupling.

The pressure in the high-pressure line is in the range from 200 to 300 bars while the pressure in the medium-pressure line is about 4 to 10 bars.

The embodiment of a pressure supply and distribution system for a compressed air breathing apparatus described below discloses other characteristics and advantageous improvements of the invention.

An embodiment of the invention is explained in greater detail below with reference to the figures. Wherein.

Figure 1:
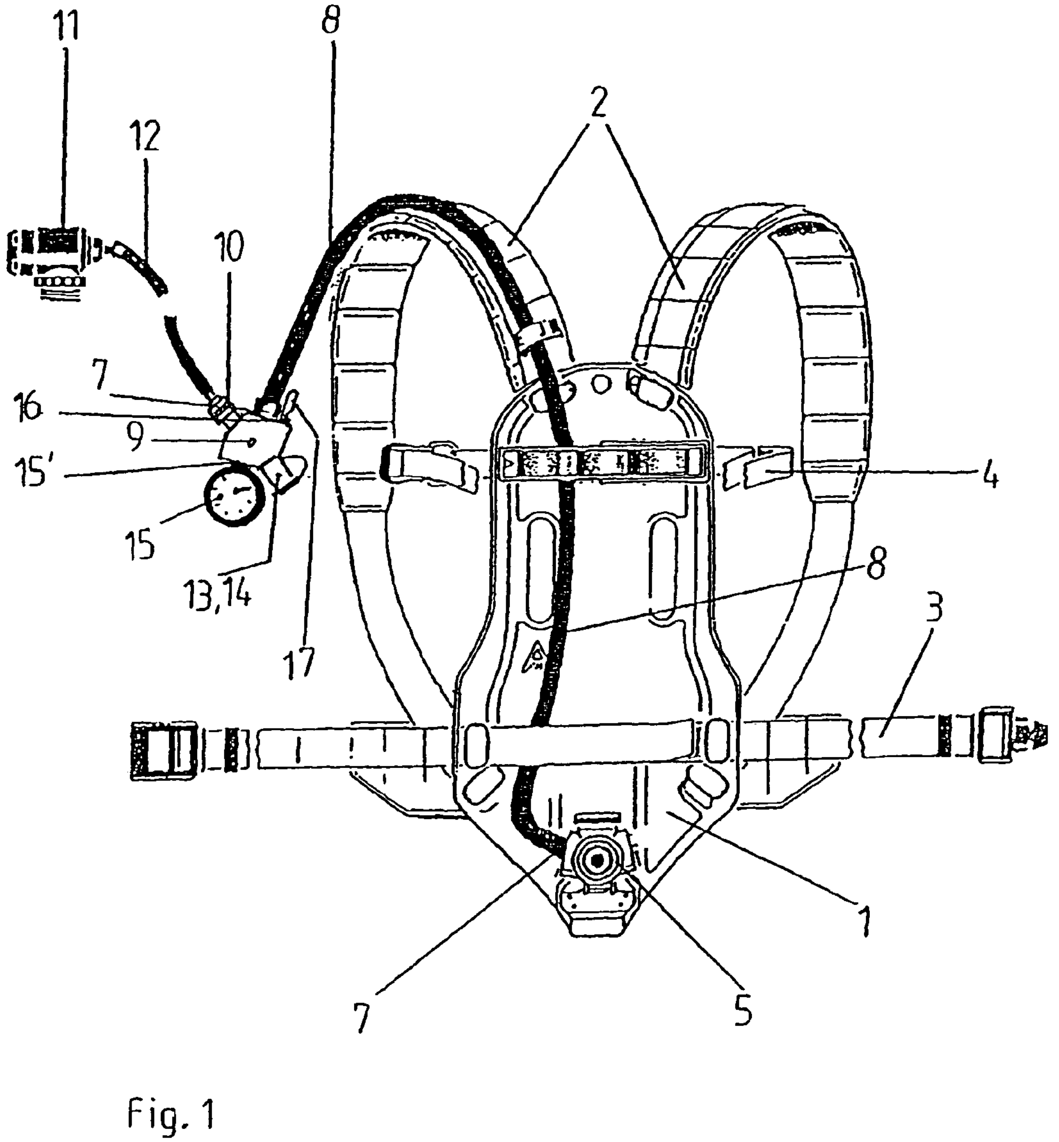
FIG. 1 shows a supporting plate of a compressed air breathing apparatus comprising the required components for connecting compressed air and distributing it.

A pressure reducer 5 is attached to the bottom of the supporting plate 1 shown in FIG. 1 with two back straps 2 and a waist strap 3 with which the plate is fixed on the wearer and with a tensioning strap 4 for attaching a compressed air bottle (not shown). A portion of the air that is supplied at high pressure is expanded to a medium pressure in the pressure reducer 5 connected to the compressed air bottle The air at a medium pressure of 10 bars and the air at a high pressure of 300 bars flows from the manifold body 6 of the pressure reducer and a coupling 7 that is pivoted in it via a single-piece flexible compressed air line, that is, a single, combined 300 bars high/10 bars medium pressure line 8 that is held on one of the two back straps 2 to a manifold 9 located in the wearer's range of vision and handling (front section). In the manifold block 9, the supplied high-pressure and medium-pressure air is distributed to a first medium-pressure connection 10 for a medium-pressure line 12 connected to a lung machine 11, to a second medium-pressure connection 13 and/or a high-pressure fast-fill connection 14, to a high-pressure connection 15' for a pressure gauge 15 (or an electronic measuring unit) and a high/medium-pressure connection 16 for an alarm device, i.e., an alarm whistle 17 controlled by high-pressure and operated by medium pressure.

Wearing comfort for the user is considerably improved by providing just a single compressed air supply line in association with a manifold block 9 installed at its one end on the wearer's front that houses all required high and medium-pressure connections, particularly as the ends of the combined single-piece high and medium-pressure line 8 are rotatably connected to the manifold body 6 of the pressure reducer 5 or the manifold block 9. This means that the compressed air supply line cannot become distorted. This greatly reduces the wearer's risk to get caught or be otherwise impaired by a multitude of straps and connecting lines. Handling and use of the breathing apparatus are simple and safe as the pressure gauge 15 and the alarm whistle 17 are located on a joint carrier (manifold block 9) in the wearer's immediate range of vision and hearing.

Figure 2:
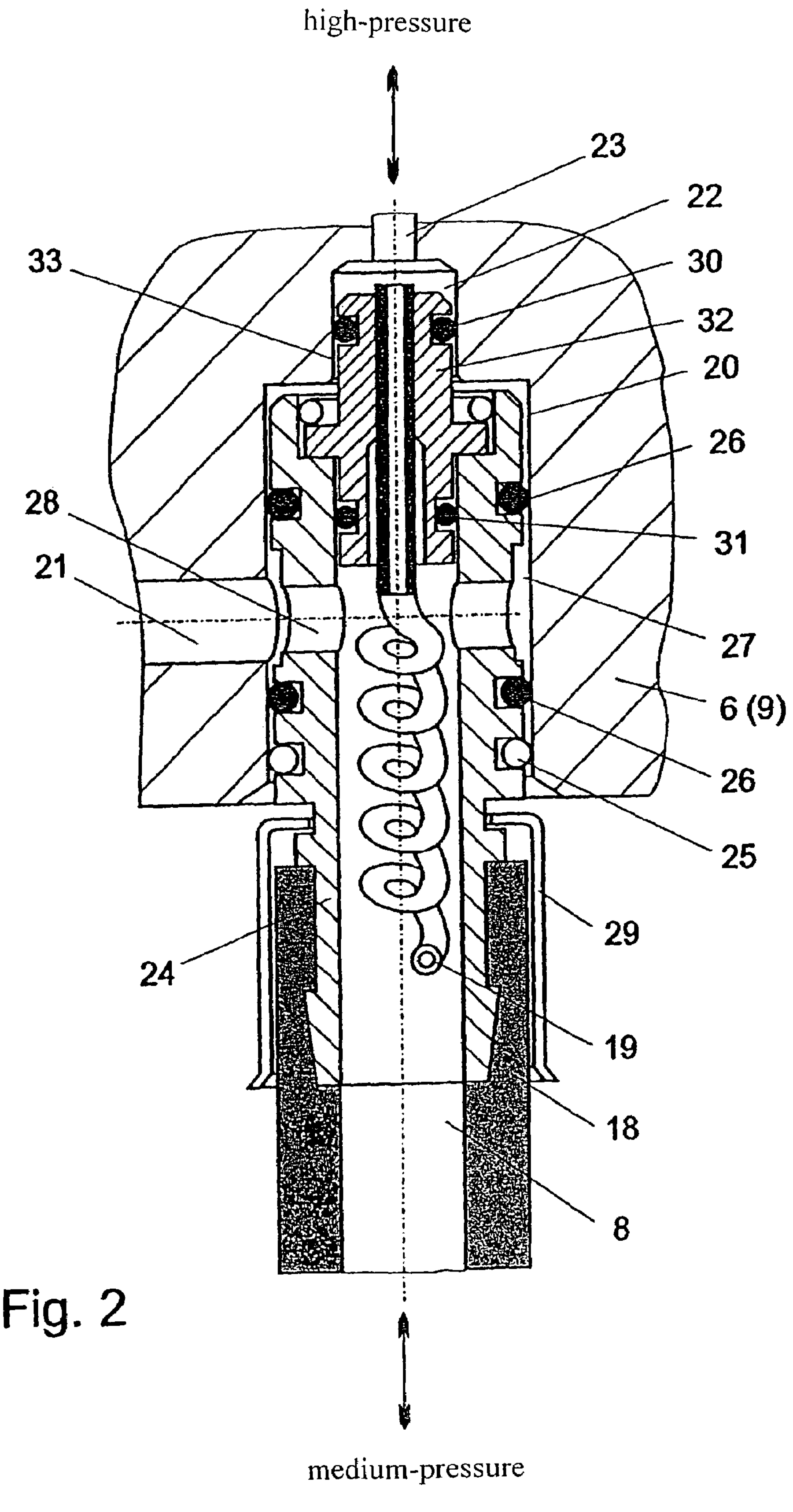
FIG. 2 shows a detailed sectional view of the design of a common high and medium-pressure line and a pivotable coupling to an air manifold block and a pressure reducer.
Figure 3:
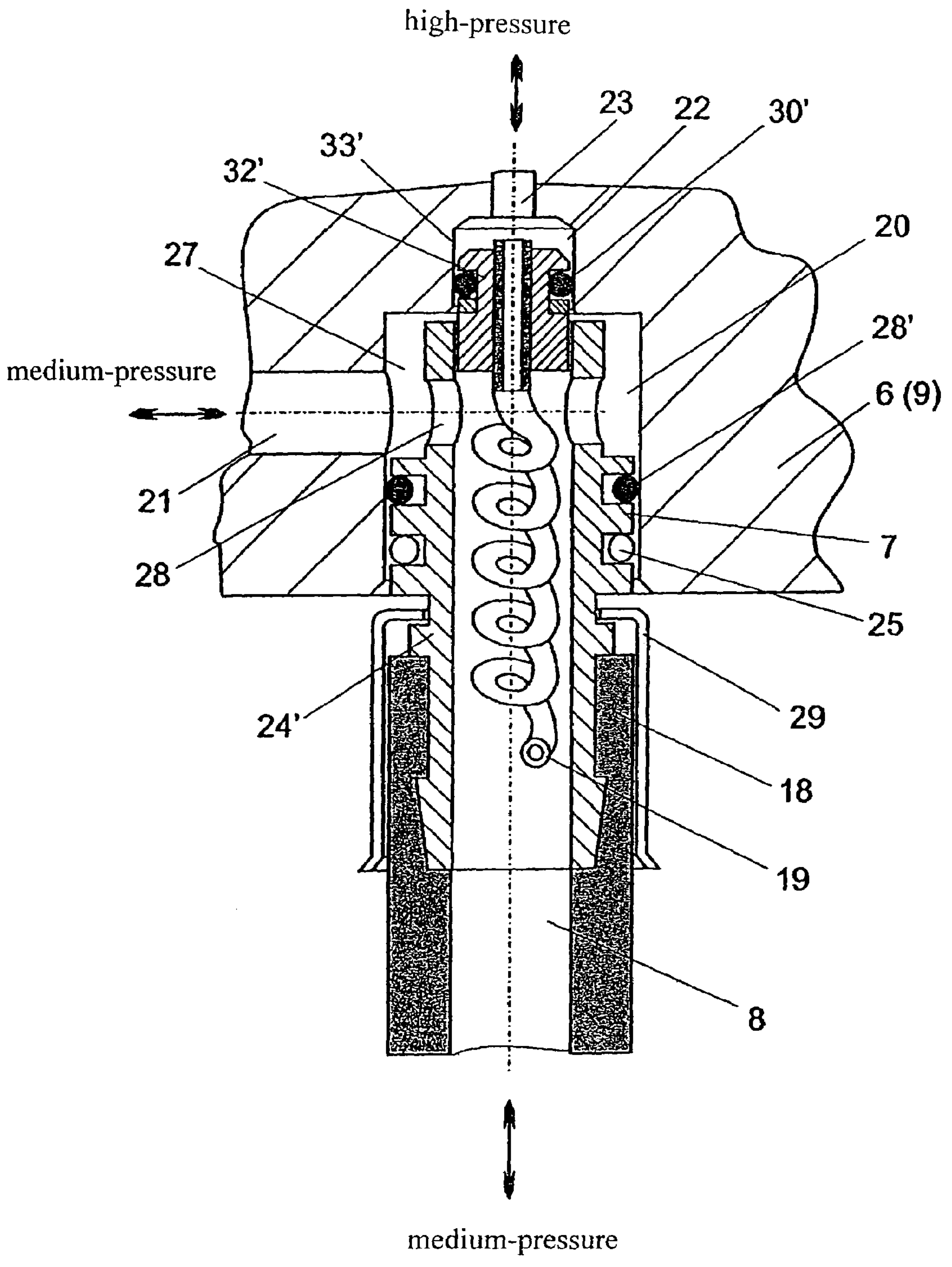
FIG. 3 shows another embodiment of the coupling for pivotable connection of the combined high/medium-pressure line to the manifold block or pressure reducer, respectively.

As can be seen from FIGS. 2 and 3, a combined high/medium-pressure line 8 consists of a flexible 10 bar medium-pressure elastomer hose 18 and a 300 bar high-pressure line 19 made of high-strength material such as a copper alloy or Teflon that is coaxially located inside said hose. The high-pressure line 19 in this embodiment is spirally wound pipe with a small diameter and therefore highly elastic so that the combined high/medium-pressure line 8 as a whole is also flexible.

It is a decisive advantage that the single high/medium-pressure line, here designed as a coaxial line, is connected to the manifold body 6 and the manifold block 9 so that it can rotate in axial direction. For this purpose, a first bearing cylinder 20 with a medium-pressure duct 21 connected to it in radial direction and a second bearing cylinder 22 stretching from the bottom of the first bearing cylinder 20 with a high-pressure duct 23 running into it in axial direction are provided in the manifold body 6/manifold block 9. The first bearing cylinder 20 comprises a pivoted medium-pressure connecting nozzle 24 that is locked in axial direction by a linch pin and sealed against the outside and against the high-pressure duct 23 by an O-ring 26. The medium-pressure connecting nozzle 24 comprises an annular groove 27 around its perimeter and a radial through hole 28 at the level of the medium-pressure duct 21. In this way, compressed air supplied via the medium-pressure duct 21 can flow through the annular groove 27 and the through hole 28 into the medium-pressure connecting nozzle 24 for the and into the medium-pressure hose 18 of the high/medium-pressure line 8.

The medium-pressure hose 18 (elastomer hose) is attached with a press sleeve 29 to the portion of the medium-pressure connecting nozzle 24 that protrudes from the manifold body 6 or manifold block 9, respectively. The spirally wound high-pressure line 19 inside the medium-pressure hose 18 is connected via a pivoted high-pressure connecting nozzle 32 sealed with O-rings 30, 31 inside the bearing cylinder 22 and the medium-pressure connecting nozzle 24. A flexible and axially rotatable compressed air line (combined high/medium-pressure line 8) that cannot twist and improves the wearing comfort of the compressed air breathing apparatus is thus provided for conveying high-pressure air between the manifold body 6 of the pressure reducer 5 and the manifold block 9 on the wearer's front. Another advantage of the combined high/medium-pressure line 8 is that the medium-pressure hose 18 encompasses and thus protects the internal high-pressure line 19. If the high-pressure line 19 breaks, the leaking air does not immediately escape into the open air but flows into the medium-pressure hose that is connected to the lung machine. The wearer can still inhale and exhale the air which is only discharged in the event of greater leakages via a pressure relief valve.

FIG. 3 shows an embodiment in which the combined coaxial high/medium-pressure line 8 is incorporated into the manifold body 6 or the manifold block 9 so that it can rotate in axial direction. In this case the medium-pressure connecting nozzle 24' has a reduced diameter in its entire upper section in the vicinity of the medium-pressure duct 21 and the high-pressure connecting nozzle 32' is firmly integrated into the medium-pressure connecting nozzle 24' so that only one O-ring 28' and 301 is required for the first and second bearing cylinders 20 and 22.

List of reference symbols

| | | |
|---|---|---|
| 1 | support plate | |
| 2 | back strap | |
| 3 | waist strap | |
| 4 | tensioning strap | |
| 5 | pressure reducer | |
| 6 | manifold body | |
| 7 | rotary coupling | |
| 8 | combined, single-piece high/medium-pressure line (coaxial line) | |
| 9 | manifold block | |
| 10 | first medium-pressure connection | |
| 11 | lung machine | |
| 12 | medium-pressure line | |
| 13 | second medium-pressure connection | |
| 14 | high-pressure fast-fill connection | |
| 15 | pressure gauge | |
| 15' | high-pressure connection | |
| 16 | combo high/medium-pressure connection | |
| 17 | alarm whistle | |
| 18 | 10 bar medium pressure hose | single-piece high-/medium-pressure line |
| 19 | 300 bar high-pressure line | |
| 20 | first bearing cylinder | |
| 21 | medium-pressure duct | |
| 22 | second bearing cylinder | |
| 23 | high-pressure duct | |
| 24, 24' | medium-pressure connecting nozzle | |
| 25 | linch pin | |
| 26 | O-ring | |
| 27 | annular groove | |
| 27' | reduced diameter section | |
| 28, 28' | through hole | |
| 29 | press sleeve | |
| 30, 30' | O-ring | |
| 31 | O-ring | |
| 32, 32' | high-pressure connecting nozzle | |
| 33, 33' | central hole | |

The invention claimed is:

1. A compressed air supply system for a compressed air breathing apparatus with a pressure reducer connected to a compressed air bottle and pressure lines connected to high-pressure and medium-pressure outputs of said pressure reducer and to a lung machine and other alarm and measuring devices and other devices, wherein the compressed air supply system comprises a combined single-piece high/medium-pressure line consisting of a medium-pressure hose containing respiratory air and having a cross section in accordance with a need for respiratory air, and a coaxial flexible high-pressure line located inside said medium-pressure hose that is connected via a rotary coupling to the pressure reducer and a manifold block for the supplied high and medium-pressure air located at a wearer's front so that it can rotate in an axial direction.

2. The compressed air supply system according to claim 1, wherein the manifold block comprises a first medium-pressure connection for the lung machine, a high-pressure connection for a pressure gauge, a combined high/medium-pressure connection for controlling an alarm whistle at high pressure and for operating it at medium pressure, a high-pressure fast-fill connection, and a second medium-pressure connection.

3. The compressed air supply system according to claim 1, wherein the flexible medium-pressure hose consists of an elastomer and the flexible high-pressure line consists of a spirally wound pipe made of a high-strength material.

4. The compressed air supply system according to claim 3, wherein the high-pressure line consists of a copper alloy or a compression-resistant synthetic material.

5. The compressed air supply system according to claim 1, wherein the manifold body of the pressure reducer and the manifold block form a first bearing cylinder (20) with a radially entering medium-pressure duct and a second bearing cylinder with an axially entering high-pressure duct following the first in an axial direction, the rotary coupling consists of a medium-pressure connecting nozzle and a high-pressure, connecting nozzle held inside said medium-pressure nozzle and sealed against it, and the medium-pressure connecting nozzle is pivoted in the first bearing cylinder and the high-pressure connecting nozzle is sealed and pivoted in the second bearing cylinder, wherein the medium-pressure connecting nozzle comprises a reduced diameter section with a through hole for supplying medium-pressure air at the level of the medium-pressure duct, and the high-pressure connecting nozzle has a central hole to receive the high-pressure line for supplying high-pressure air.

6. The compressed air supply system according to claim 5, wherein the high-pressure connecting nozzle is pivotably held in the medium-pressure connecting nozzle, one O-ring each is located inside that nozzle and in the second bearing cylinder, and the reduced diameter section is designed as an annular groove with O-rings on top and underneath.

7. The compressed air supply system according to claim 5, wherein the high-pressure connecting nozzle is firmly linked with the medium-pressure connecting nozzle and one O-ring each is placed in the section of the second bearing cylinder as well as below the reduced diameter section of the medium-pressure connecting nozzle.

8. The compressed air supply system according to claim 5, wherein the high-pressure line is fastened in an axial hole of the high-pressure connecting nozzle.

9. The compressed air supply system according to claim 5, wherein the medium-pressure hose is attached to the portion of the medium-pressure connecting nozzle that protrudes from the first bearing cylinder using a press sleeve.

10. The compressed air supply system according to claim 5, wherein the medium-pressure connecting nozzle is held in the manifold body or the manifold block, respectively, by a linch pin.

11. The compressed air supply system according to claim 1, wherein the flexible medium-pressure hose consists of an elastomer and the flexible high-pressure line consists of a spirally wound pipe made of a high-strength material.

12. The compressed air supply system according to claim 11, wherein the high-pressure line consists of a copper alloy or a compression-resistant synthetic material.

13. The compressed air supply system according to claim 6, wherein the high-pressure line is fastened in an axial hole of the high-pressure connecting nozzle.

14. The compressed air supply system according to claim 7, wherein the high-pressure line is fastened in an axial hole of the high-pressure connecting nozzle.

15. The compressed air supply system according to claim 6, wherein the medium-pressure hose is attached to the portion of the medium-pressure connecting nozzle that protrudes from the first bearing cylinder using a press sleeve.

16. The compressed air supply system according to claim 7, wherein the medium-pressure hose is attached to the portion of the medium-pressure connecting nozzle that protrudes from the first bearing cylinder using a press sleeve.

17. The compressed air supply system according to claim 8, wherein the medium-pressure hose is attached to the portion of the medium-pressure connecting nozzle that protrudes from the first bearing cylinder using a press sleeve.

18. The compressed air supply system according to claim 13, wherein the medium-pressure hose is attached to the portion of the medium-pressure connecting nozzle that protrudes from the first bearing cylinder using a press sleeve.

19. The compressed air supply system according to claim 14, wherein the medium-pressure hose is attached to the portion of the medium-pressure connecting nozzle that protrudes from the first bearing cylinder using a press sleeve.

20. The compressed air supply system according to claim 6, wherein the medium-pressure connecting nozzle is held in the manifold body or the manifold block, respectively, by a linch pin.

21. The compressed air supply system according to claim 7, wherein the medium-pressure connecting nozzle is held in the manifold body or the manifold block, respectively, by a linch pin.

22. The compressed air supply system according to claim 8, wherein the medium-pressure connecting nozzle is held in the manifold body or the manifold block, respectively, by a linch pin.

23. The compressed air supply system according to claim 9, wherein the medium-pressure connecting nozzle is held in the manifold body or the manifold block, respectively, by a linch pin.

24. The compressed air supply system according to claim 13, wherein the medium-pressure connecting nozzle is held in the manifold body or the manifold block, respectively, by a linch pin.

25. The compressed air supply system according to claim 14, wherein the medium-pressure connecting nozzle is held in the manifold body or the manifold block, respectively, by a linch pin.

26. The compressed air supply system according to claim 15, wherein the medium-pressure connecting nozzle is held in the manifold body or the manifold block, respectively, by a linch pin.

27. The compressed air supply system according to claim 16, wherein the medium-pressure connecting nozzle is held in the manifold body or the manifold block, respectively, by a linch pin.

28. The compressed air supply system according to claim 17, wherein the medium-pressure connecting nozzle is held in the manifold body or the manifold block, respectively, by a linch pin.

29. The compressed air supply system according to claim 18, wherein the medium-pressure connecting nozzle is held in the manifold body or the manifold block, respectively, by a linch pin.

30. The compressed air supply system according to claim 19, wherein the medium-pressure connecting nozzle is held in the manifold body or the manifold block, respectively, by a linch pin.

31. The compressed air supply system according to any one of claims 5 through 10 and 13-30, wherein the pressure of the high-pressure air is in the range of about 200 to 300 bars and the pressure of the medium-pressure air is in the range of about 4 to 10 bars.

* * * * *